United States Patent
Fiebig et al.

(10) Patent No.: US 12,268,388 B2
(45) Date of Patent: Apr. 8, 2025

(54) SURGICAL STAPLER CARTRIDGE WITH INTEGRATED RFID FEATURE

(71) Applicant: Cilag GmbH International, Zug (CH)

(72) Inventors: Kevin M. Fiebig, Cincinnati, OH (US); Nicholas Fanelli, Morrow, OH (US); Shane R. Adams, Lebanon, OH (US); Taylor W. Aronhalt, Loveland, OH (US)

(73) Assignee: Cilag GmbH International, Zug (CH)

( * ) Notice: Subject to any disclaimer, the term of this patent is extended or adjusted under 35 U.S.C. 154(b) by 211 days.

(21) Appl. No.: 17/695,468

(22) Filed: Mar. 15, 2022

(65) Prior Publication Data

US 2023/0293172 A1 Sep. 21, 2023

(51) Int. Cl.
*A61B 17/072* (2006.01)
*A61B 90/98* (2016.01)

(52) U.S. Cl.
CPC ............ *A61B 17/072* (2013.01); *A61B 90/98* (2016.02); *A61B 2017/07257* (2013.01); *A61B 2017/07271* (2013.01); *A61B 2017/07278* (2013.01)

(58) Field of Classification Search
CPC ............ A61B 17/072; A61B 17/07207; A61B 2017/07271; A61B 2017/07278; A61B 90/98; A61B 2090/38; A61B 2017/07257
USPC ............................................ 227/178.1, 176.1
See application file for complete search history.

(56) References Cited

U.S. PATENT DOCUMENTS

| | | |
|---|---|---|
| 7,404,508 B2 | 7/2008 | Smith et al. |
| 7,434,715 B2 | 10/2008 | Shelton, IV et al. |
| 7,644,848 B2 * | 1/2010 | Swayze ................. A61B 34/76 227/19 |
| 7,721,930 B2 | 5/2010 | McKenna et al. |
| 7,959,050 B2 | 6/2011 | Smith et al. |
| 8,210,411 B2 | 7/2012 | Yates et al. |
| 8,408,439 B2 | 4/2013 | Huang et al. |
| 8,453,914 B2 | 6/2013 | Laurent et al. |

(Continued)

FOREIGN PATENT DOCUMENTS

| | | |
|---|---|---|
| EP | 1943976 A2 | 7/2008 |
| EP | 3756579 A2 | 12/2020 |
| EP | 3838172 A1 | 6/2021 |

OTHER PUBLICATIONS

Pocket—definition, by Collins. URL https://www.collinsdictionary.com/us/dictionary/english/pocket , retrieved on Feb. 6, 2024 (Year: 2024).*

(Continued)

*Primary Examiner* — Robert F Long
*Assistant Examiner* — Eduardo R Ferrero
(74) *Attorney, Agent, or Firm* — Frost Brown Todd LLP

(57) ABSTRACT

A staple cartridge including a cartridge body and a first RFID feature. The cartridge body defines a longitudinal axis extending from a proximal end to a distal end of the cartridge body. The cartridge body is configured to be received within a jaw of a surgical stapler. The cartridge body also defines a plurality of staple apertures that are configured to house staples. The proximal portion of the cartridge body defines a pocket, and the pocket is proximal to a proximal most staple aperture of the plurality of staple apertures. The first RFID feature is fixed within the pocket. The first RFID feature is configured to communicate with a second RFID feature presented by the jaw of the surgical stapler.

16 Claims, 18 Drawing Sheets

(56) References Cited

U.S. PATENT DOCUMENTS

| | | |
|---|---|---|
| 9,171,244 B2 | 10/2015 | Endou et al. |
| 9,186,142 B2 | 11/2015 | Fanelli et al. |
| 9,517,065 B2 | 12/2016 | Simms et al. |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 10,092,292 B2 | 10/2018 | Boudreaux et al. |
| 11,540,826 B2 | 1/2023 | Nalagatla et al. |
| 2009/0057369 A1* | 3/2009 | Smith ............... A61B 17/07207 227/175.1 |
| 2015/0053743 A1 | 2/2015 | Yates et al. |
| 2017/0296189 A1* | 10/2017 | Vendely ............... A61B 17/105 |
| 2019/0200986 A1* | 7/2019 | Shelton, IV ......... A61B 5/4848 |
| 2020/0405436 A1* | 12/2020 | Shelton, IV ........... A61B 90/98 |
| 2020/0405438 A1* | 12/2020 | Shelton, IV ......... A61B 17/072 |
| 2021/0059674 A1* | 3/2021 | Shelton, IV ......... A61B 5/4848 |
| 2021/0236123 A1 | 8/2021 | Hessler et al. |
| 2022/0104813 A1* | 4/2022 | Shelton, IV ......... A61B 17/072 |
| 2023/0293172 A1* | 9/2023 | Fiebig .............. A61B 17/07207 227/178.1 |

OTHER PUBLICATIONS

Pocket—definition, by Merriam-Webster. URL https://www.merriam-webster.com/dictionary/pocket , retrieved on Feb. 6, 2024 (Year: 2024).*

Present—definition, by Merriam-Webster. URL https://www.merriam-webster.com/dictionary/present , retrieved on Feb. 6, 2024 ( Year: 2024).*

International Search Report and Written Opinion dated Jul. 21, 2023, for International Application No. PCT/IB2023/052380, 17 pages.

* cited by examiner

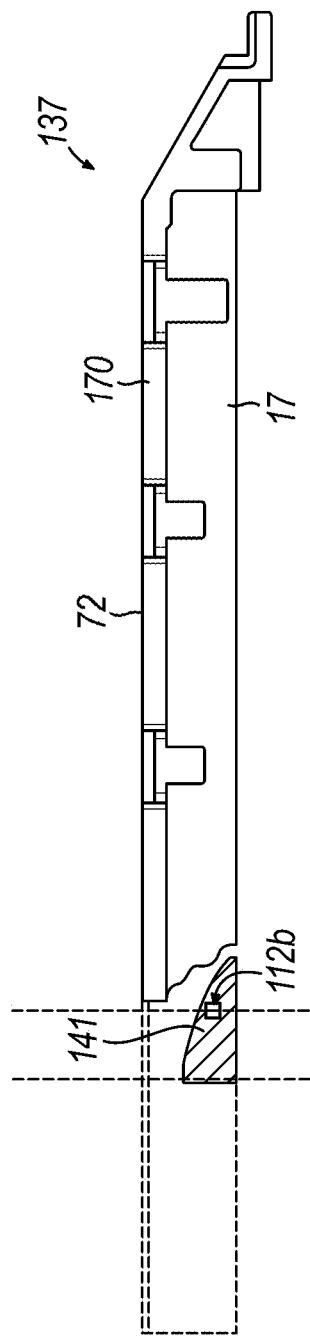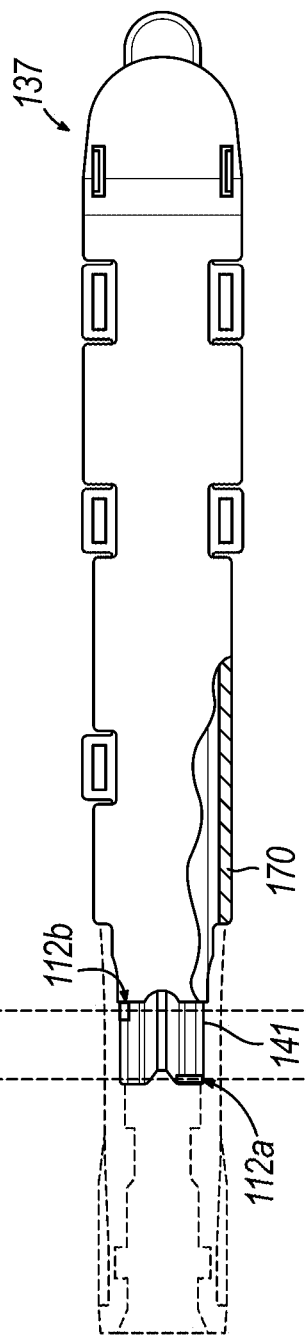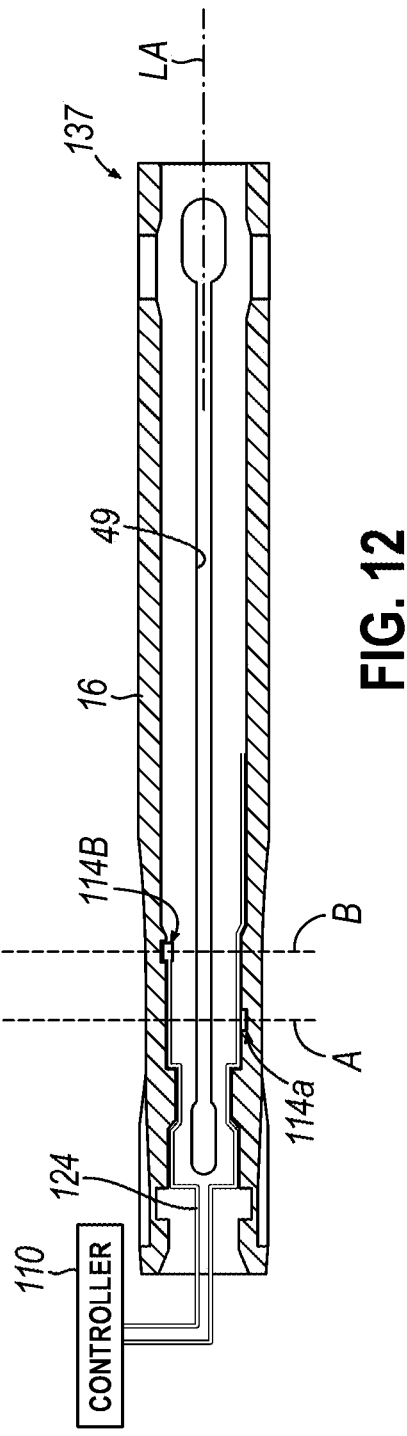

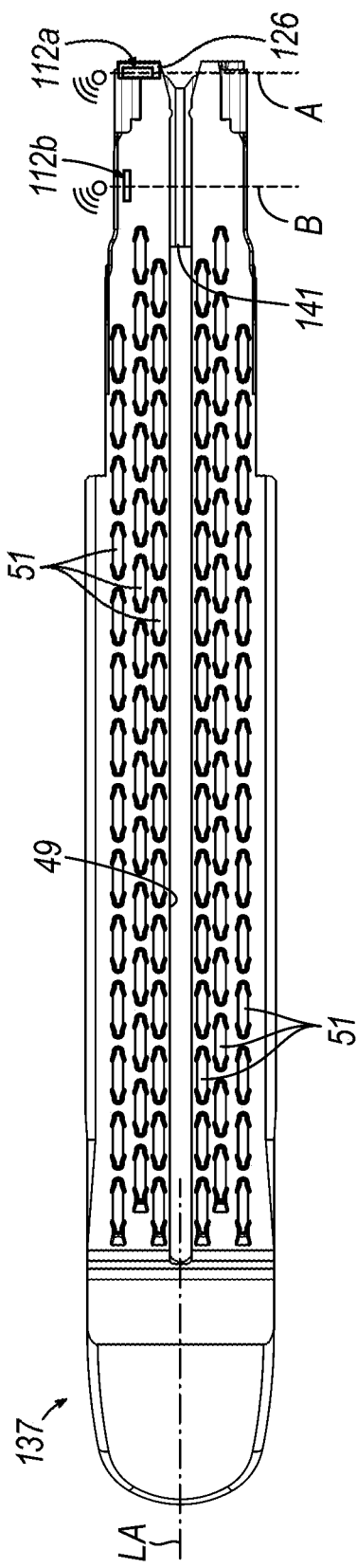
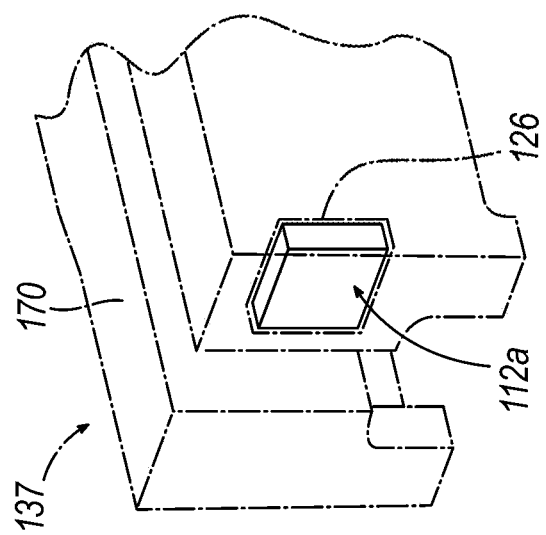
FIG. 13
FIG. 14

SURGICAL STAPLER CARTRIDGE WITH INTEGRATED RFID FEATURE

BACKGROUND

Examples of surgical instruments include surgical staplers, which may be configured for use in laparoscopic surgical procedures and/or open surgical procedures. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein in its entirety.

In various embodiments, radio-frequency identification ("RFID") technology can be used to identify the components of a surgical instrument, such as staple cartridges, for example. Examples of surgical systems which use RFID technology can be found in the disclosures of U.S. Pat. No. 7,959,050, entitled "Electrically Self-powered Surgical Instrument with Manual Release," which issued on Jun. 14, 2011; U.S. Patent Application No. 2015/0053743, entitled "Error Detection Arrangements for Surgical Instrument Assemblies," which published on Feb. 26, 2015, now abandoned; and U.S. Pub. No. 2020/0405436, entitled "Surgical Instrument System Comprising an RFID System," published Dec. 31, 2020, issued as U.S. Pat. No. 11,376,098 on Jul. 5, 2022, all of which are incorporated by reference herein in their entireties.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 10 depicts a side view of an exemplary staple cartridge fitted with a cover configured to be installed within the surgical stapling instrument of FIG. 8, with a portion of the staple cartridge shown in a cross-sectional view to show additional detail;

FIG. 11 depicts a top view of the staple cartridge and the cover of FIG. 9 with a portion of the staple cartridge shown in a cross-sectional view to show additional detail;

FIG. 12 depicts a cross-sectional top plan view of a lower jaw of the end effector of FIG. 8 configured to receive the staple cartridge of FIG. 9;

FIG. 13 depicts a top view of the staple cartridge of FIG. 9 with the cover shown in phantom lines;

FIG. 14 depicts an enlarged, perspective view of the proximal end of the staple cartridge of FIG. 9, with a portion of the staple cartridge shown in phantom to enable viewing of an RFID tag of the type shown in FIG. 9;

Figure 1:
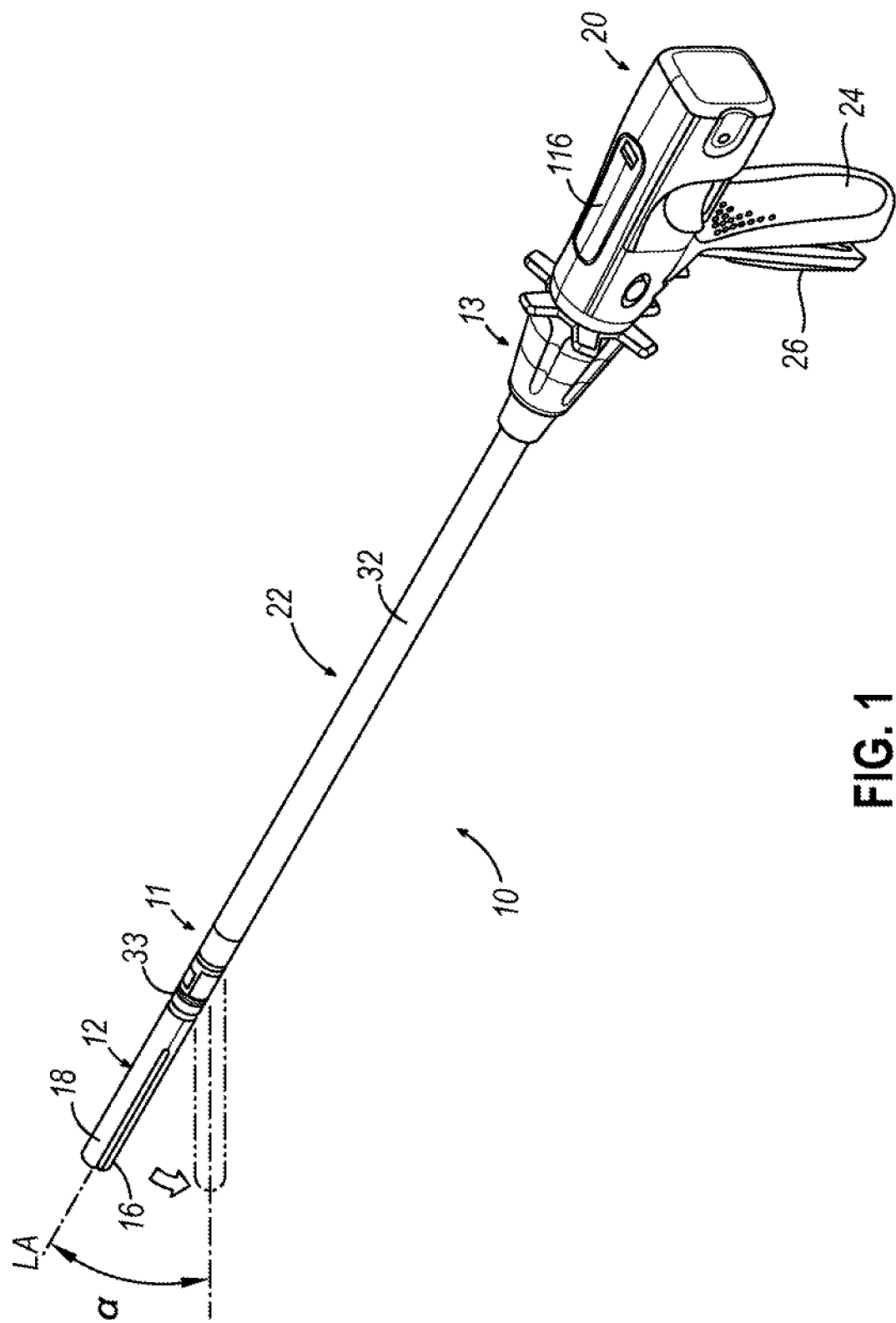
FIG. 1 depicts a perspective view of an example of an articulating surgical stapling instrument comprising a handle, a shaft, and an articulable end effector.
Figure 2:
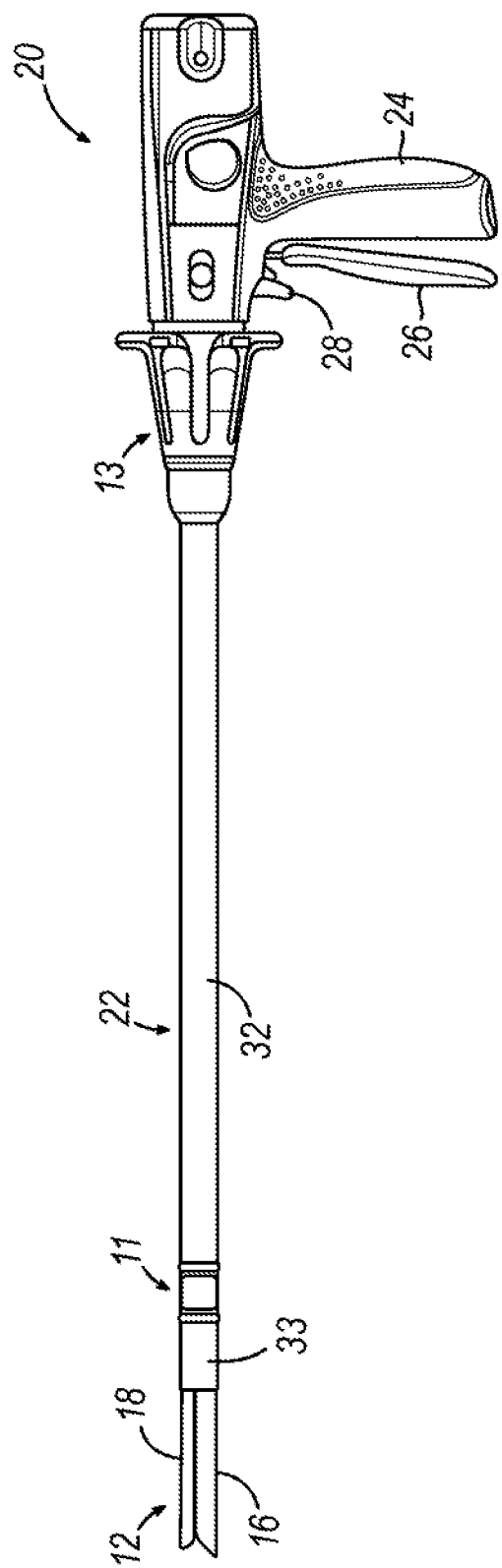
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Exemplary Surgical Stapler

FIGS. 1-7 depict an example of a surgical stapling and severing instrument (10) that is sized for insertion, in a nonarticulated state as depicted in FIG. 1, through a trocar cannula, thoracotomy, or other incision to a surgical site in a patient for performing a surgical procedure. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20).

Once articulation joint (11) and end effector (12) are inserted into the patient, articulation joint (11) may be remotely articulated, as depicted in phantom in FIG. 1, by an articulation control (13), such that end effector (12) may be deflected from a longitudinal axis (LA) of shaft (22) at a desired angle (a). By way of example only, articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety; and/or U.S. Pat. No. 9,795,379, entitled "Surgical Instrument with Multi-Diameter Shaft," issued Oct. 24, 2017, the disclosure of which is incorporated by reference herein in its entirety. Other suitable forms that articulation joint (11) and articulation control (13) may take will be apparent to those skilled in the art in view of the teachings herein.

End effector (12) of the present example includes a lower jaw (16) and an upper jaw in the form of a pivotable anvil (18). By way of example only, lower jaw (16) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (18) may be constructed and operable in accordance with at least some of the teachings of at least some of the teachings of U.S. Pat. No. 10,092,292, entitled "Staple Forming Features for Surgical Stapling Instrument," issued Oct. 9, 2018, the disclosure of which is incorporated by reference herein in its entirety. Other suitable forms that lower jaw (16) and anvil (18) may take will be apparent to those skilled in the art in view of the teachings herein.

Handle portion (20) includes a pistol grip (24) and a closure trigger (26). Closure trigger (26) is pivotable toward pistol grip (24) to cause clamping, or closing, of anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along a length of shaft (22); and closure ring (33) is positioned distal to articulation joint (11). Articulation joint (11) is operable to transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of tissue clamped in end effector (12), as will be described in greater detail below. Thereafter, triggers (26, 28) may be released to release the tissue from end effector (12).

Figure 4A:
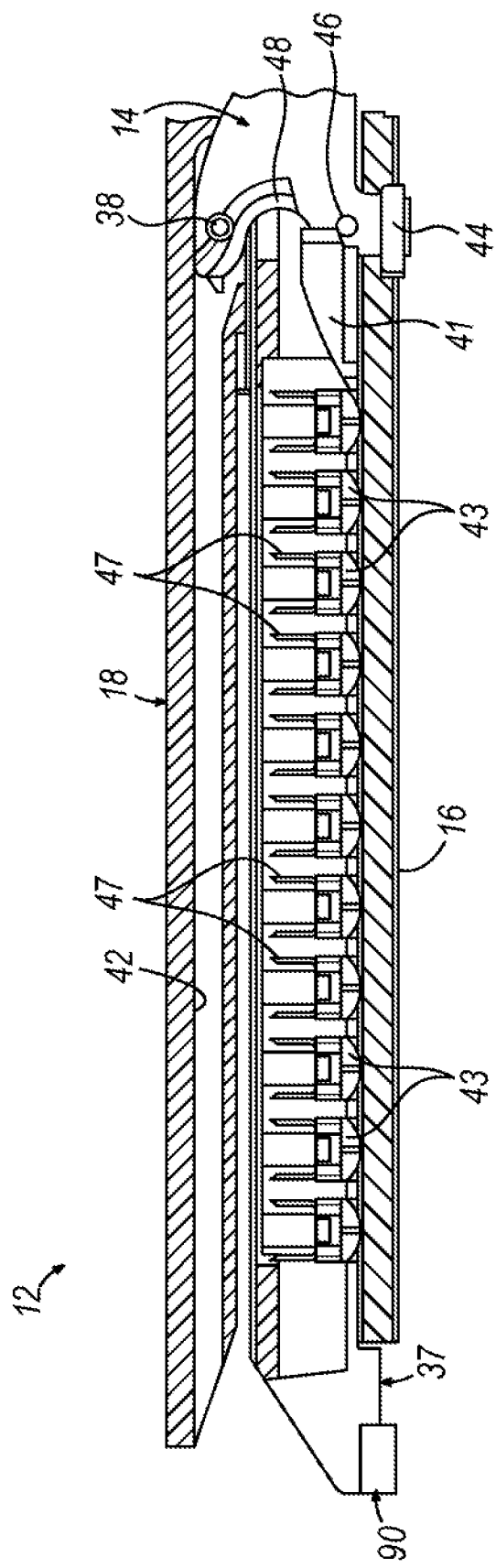
FIG. 4A depicts a side cross-sectional view of the end effector of FIG. 3, taken along line 4-4 of FIG. 3, with a firing beam in a proximal position.
Figure 4B:
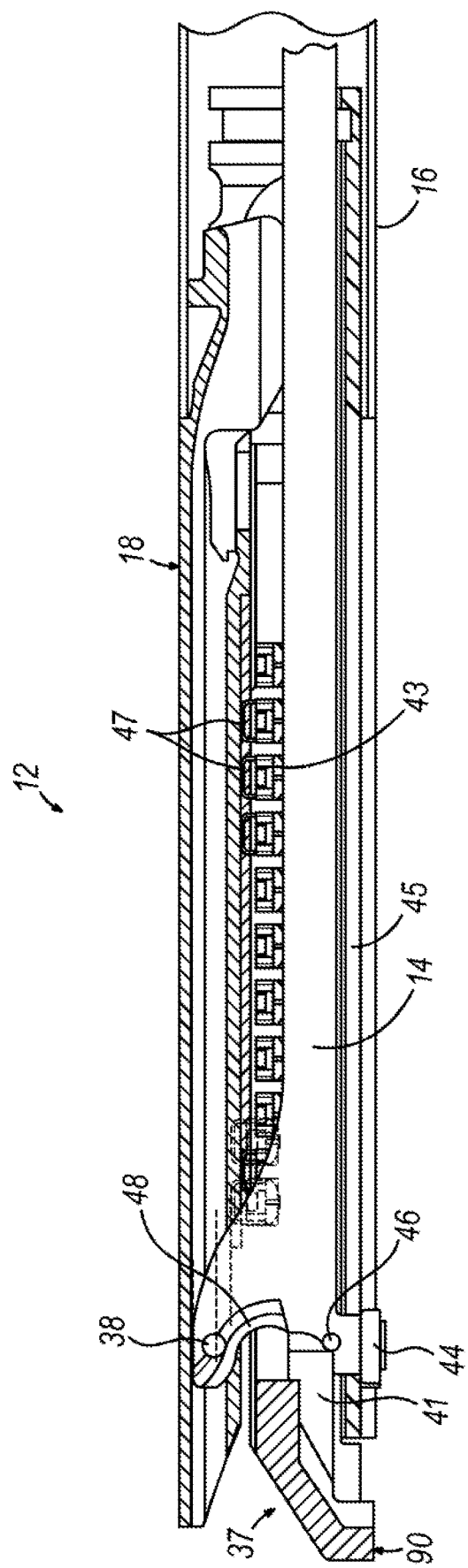
FIG. 4B depicts a side cross-sectional view of the end effector of FIG. 3, taken along line 4-4 of FIG. 3, with the firing beam in a distal position.

As best seen in FIGS. 4A-4B, firing beam (14) of the present example includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein in its entirety. Other suitable forms that firing beam (14) may take will be apparent to those skilled in the art in view of the teachings herein.

Figure 3:
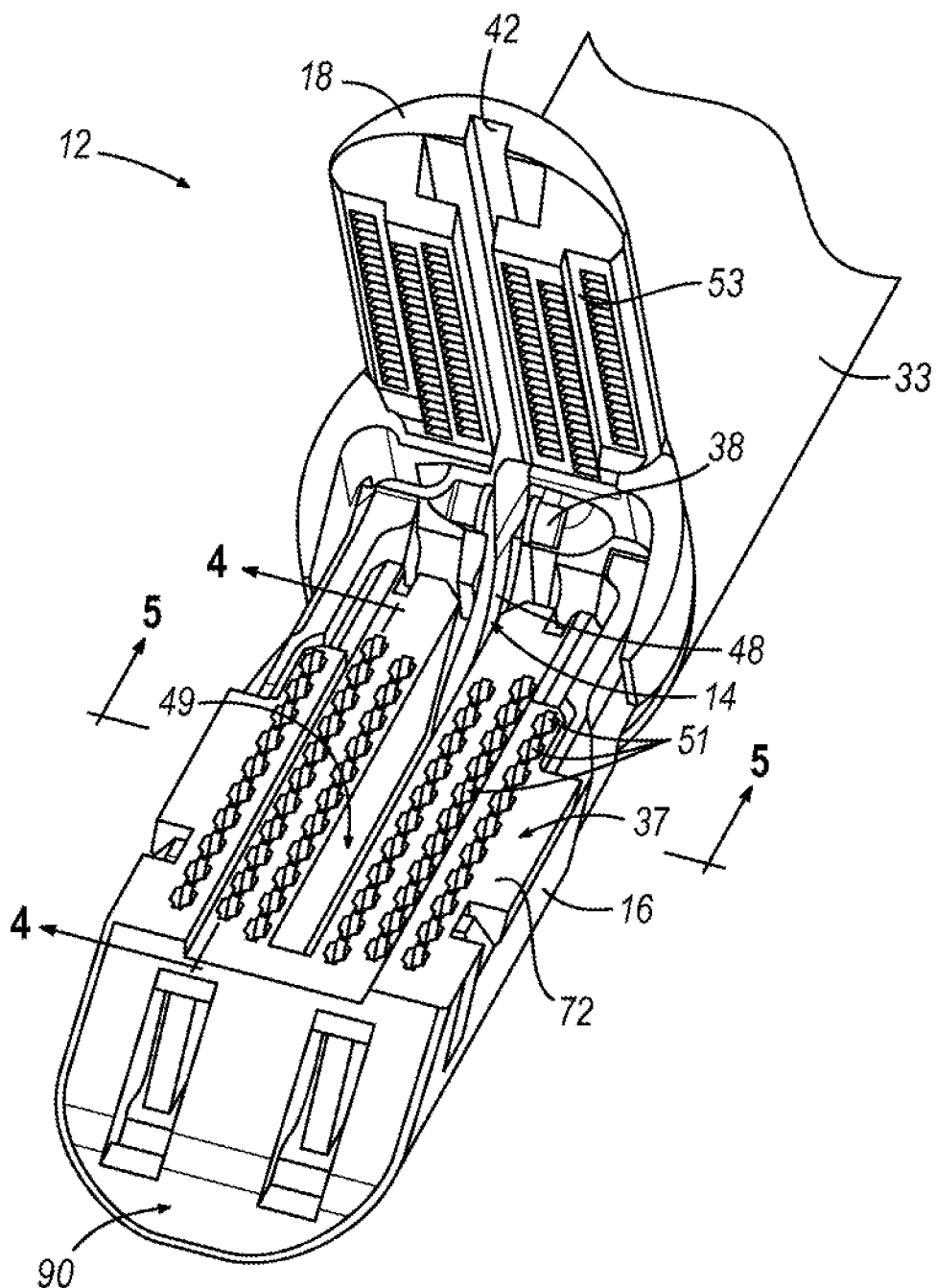
FIG. 3 depicts a perspective view of an opened end effector of the instrument of FIG. 1.
Figure 5:
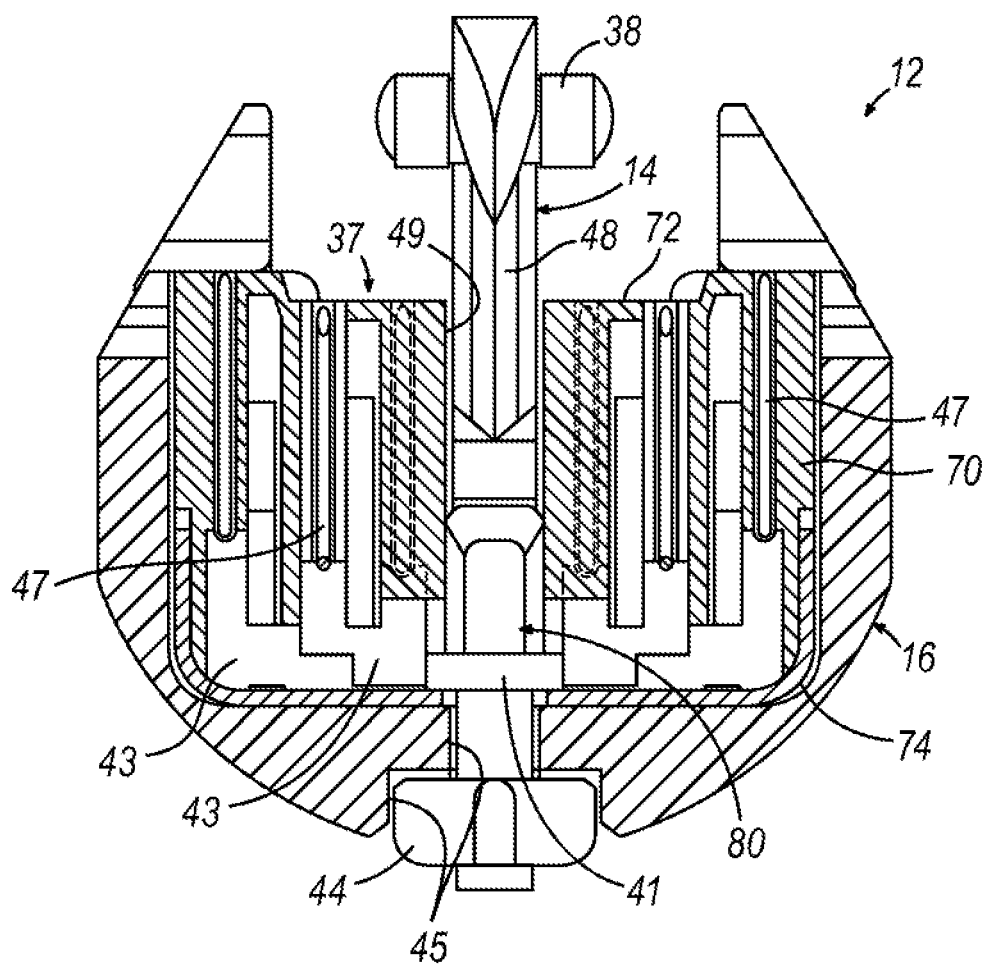
FIG. 5 depicts an end cross-sectional view of the end effector of FIG. 3, taken along line 5-5 of FIG. 3.
Figure 6:
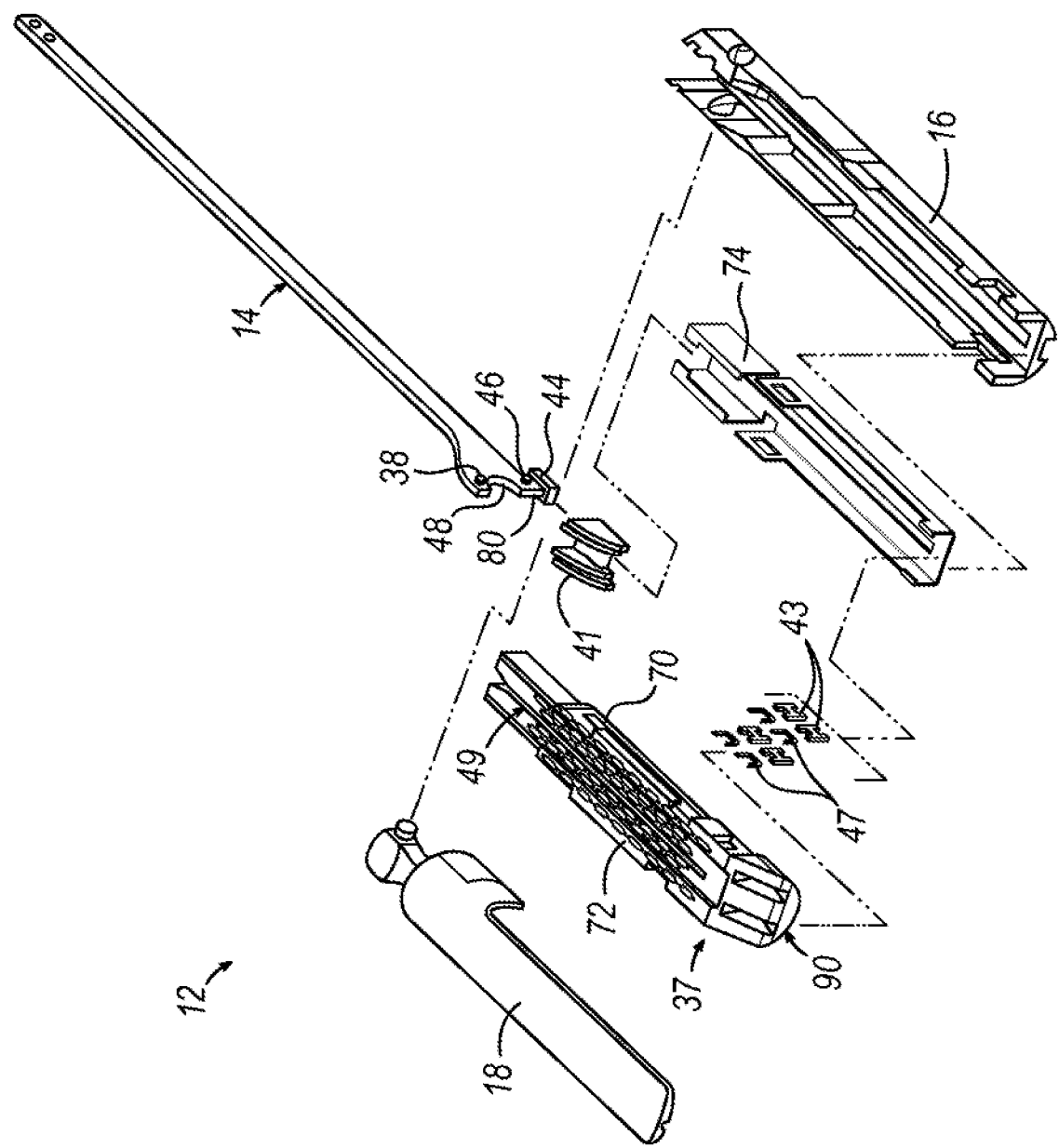
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). Three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and cartridge tray (74), with wedge sled (41) being located proximal to staple drivers (43) when staple cartridge (37) is in a pre-fired (or "unspent") state. Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

By way of example only, staple cartridge (37) may be constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein in its entirety. Other suitable forms that staple cartridge (37) may take will be apparent to those skilled in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) located at a distal end of firing beam (14) is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on an inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
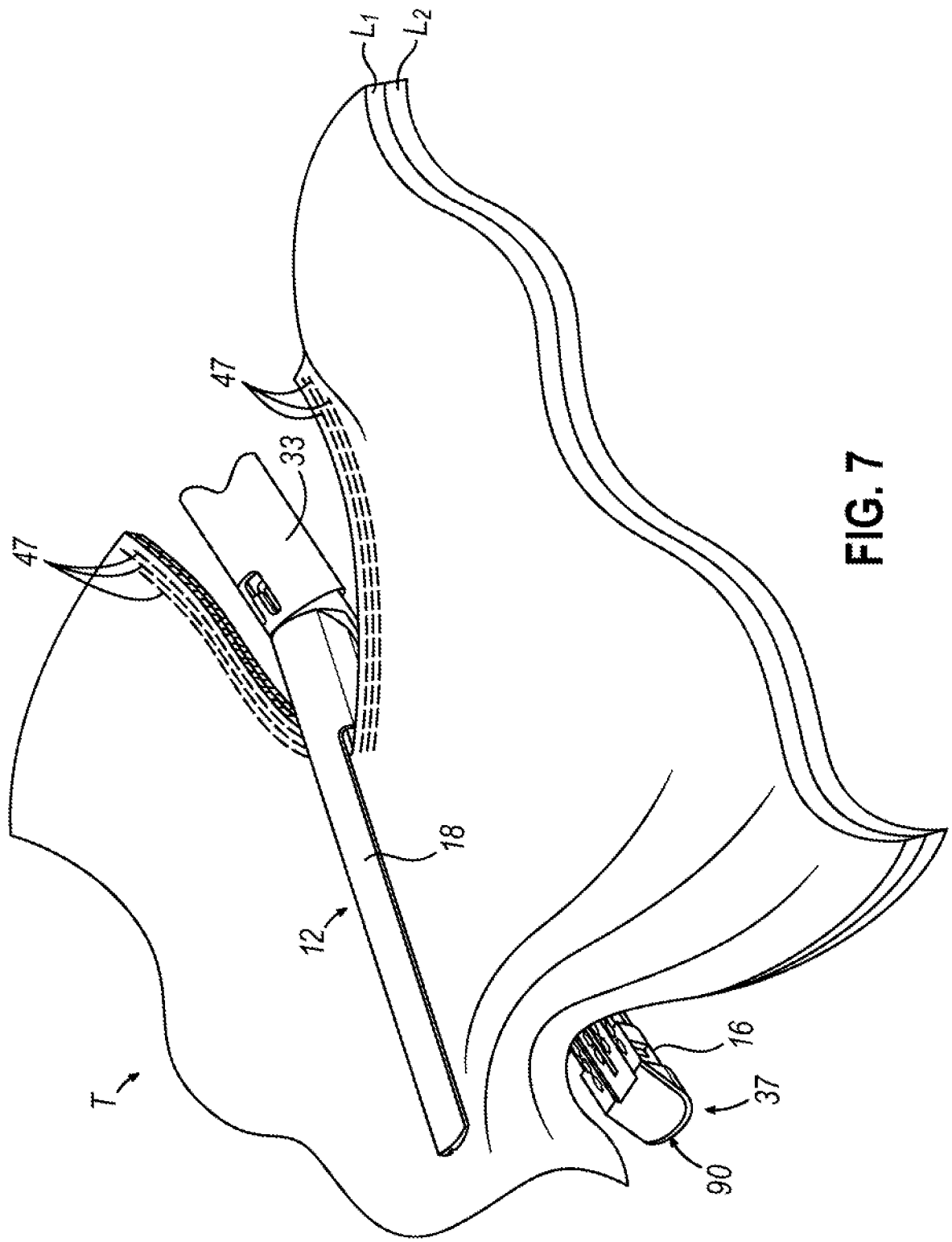
FIG. 7 depicts a perspective view of the end effector of FIG. 3, positioned at tissue and having been actuated once in the tissue.

FIG. 7 shows end effector (12) having been actuated through a single stroke through layers ($L_1$, $L_2$) of tissue (T). As shown, cutting edge (48) (obscured in FIG. 7) has cut through tissue (T), while staple drivers (43) have driven three alternating rows of staples (47) through a tissue (T) on each side of a cut line produced by cutting edge (48). Staples (47) are all oriented substantially parallel to the cut line in this example, though it should be understood that staples (47) may be positioned at any suitable orientations. In the present example, end effector (12) is withdrawn from the trocar or incision after the first stroke is complete, spent staple cartridge (37) is replaced with a new staple cartridge, and end effector (12) is then again inserted through the trocar or incision to reach the stapling site for further cutting and stapling. This process may be repeated until the desired number of cuts and staples (47) have been provided. Anvil (18) may need to be closed to facilitate insertion and withdrawal through the trocar; and anvil (18) may need to be opened to facilitate replacement of staple cartridge (37).

In some versions, instrument (10) provides motorized control of firing beam (14). By way of example only, such motorization may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein in its entirety; and/or U.S. Pat. No. 8,210,411, entitled "Motor-Driven Surgical Instrument," issued Jul. 3, 2012, the disclosure of which is incorporated by reference herein in its entirety. Other suitable components, features, and configurations for providing motorization of firing beam (14) will be apparent to those skilled in the art in view of the teachings herein. It should also be understood that some other versions may provide manual driving of firing beam (14), such that a motor may be omitted.

II. Exemplary Surgical Stapler Incorporating RFID Features

In some instances, it may be desirable to provide a surgical instrument similar to instrument (10) with a radio-frequency identification ("RFID") system that is configured to identify and communicate with a staple cartridge loaded into the end effector of the surgical instrument. Such an RFID system may ensure that the loaded staple cartridge (137) is designated for use with the surgical instrument and that the staple cartridge is properly seated in the end effector jaw. Such an RFID system may thus be implemented to inform a controller (also referred to as a control circuit) of the surgical instrument whether the instrument is ready for use (e.g., whether a compatible staple cartridge has been fully seated in the end effector jaw), and the controller may then enable or inhibit firing of the instrument based on such received information. Additionally, such an RFID system may track a location of a wedge sled of a compatible staple cartridge to ensure that the firing stroke is completed, and/or to inform a user of a status of completion of the firing stroke. Exemplary versions of such an RFID system are disclosed in U.S. Pub. No. 2020/0405436, entitled "Surgical Instrument System Comprising an RFID System," issued as U.S. Pat. No. 11,376,098 on Jul. 5, 2022, incorporated by reference above. In some instances, it may be desirable to strategically construct certain components of the surgical instrument such that certain components of the RFID system do not contact metal components of the surgical instrument to thereby prevent interference with proper operation of the RFID system. Exemplary versions of such configurations are described in greater detail below.

RFID is used in a variety of industries to track and identify objects. RFID relies on radio waves to transfer digitally-stored information from an RFID transponder (also referred to as an RFID tag or chip) to an RFID reader (also referred to as an RFID sensor) or receiver configured to receive the information. RFID technology uses RFID tags, which contain electronically-stored information, and RFID readers, which serve to identify and communicate with RFID tags. There are two different types of RFID systems—active RFID systems and passive RFID systems. Active RFID systems include RFID tags that comprise an on-board power source to broadcast their signals. Active RFID tags can include a battery within RFID tag which allows active RFID tag to function independently from RFID reader. As such, RFID tags in an active RFID system do not need to wait to receive a signal from an RFID reader before sending out information. Instead, active RFID tags are free to continuously send out a signal, or beacon. Many commercially available active RFID systems often operate at one of two main frequency ranges—433 MHz and 915 MHz, but any suitable frequency range can be used. Typically, an RFID tag (112) must be within a specific distance or frequency range in order to be identified by its corresponding RFID reader.

Passive RFID systems include RFID tags which do not comprise an on-board power source but instead receive the energy needed to operate from an RFID reader. Contrary to active RFID tags, RFID tags in a passive RFID system do not actively send out a signal before receiving a prompt. Instead, passive RFID tags wait to receive information from an RFID reader before sending out a return signal. Many commercially-available passive RFID systems often operate within three frequency ranges—Low Frequency ("LF"), High Frequency ("HF") & Near-Field Communication ("NFC"), and Ultra High Frequency ("UHF"). LF bandwidth is 125-134 KHz and includes a longer wavelength with a short read range of approximately one to ten centimeters. HF and NFC bandwidth is 13.56 MHz and includes a medium wavelength with a typical read range of one centimeter to one meter. UHF bandwidth is 865-960 MHz and includes a short, high-energy wavelength of one meter which translates into a long-read range. The above being said, any suitable frequency can be used.

Figure 8:
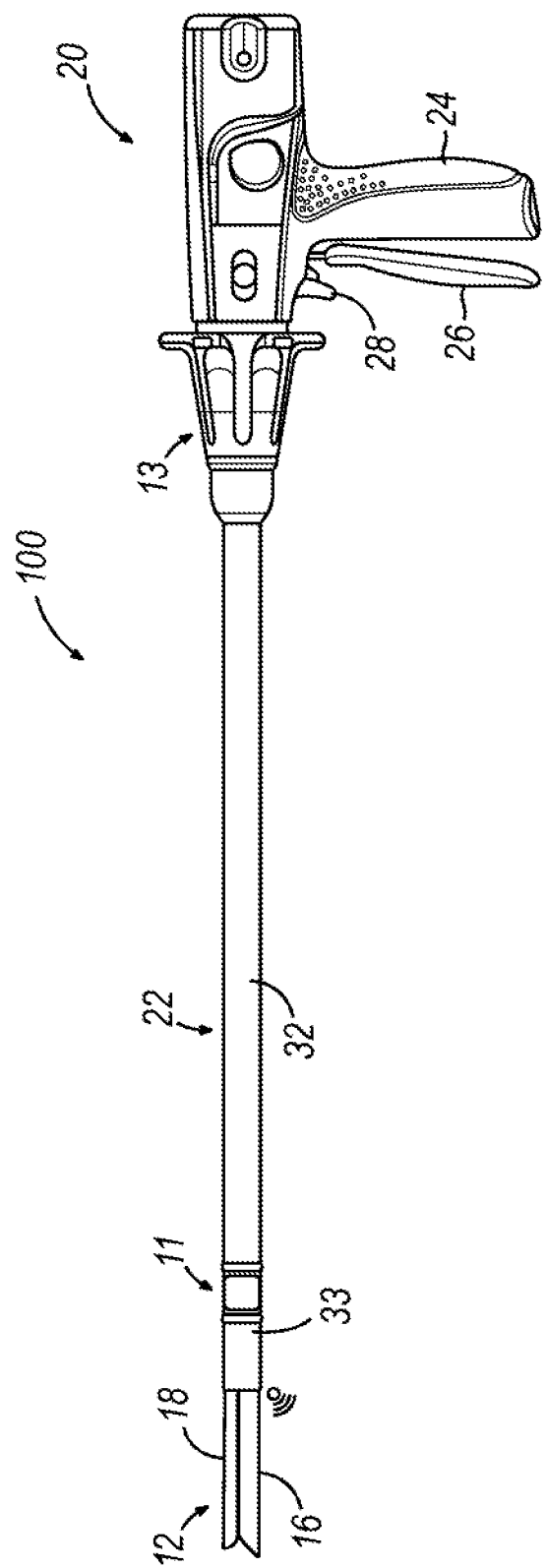
FIG. 8 depicts a side view of another exemplary articulating surgical stapling instrument, comprising a handle, a shaft, and an articulable end effector.

FIG. 8 shows a surgical instrument (100) that is similar to surgical instrument (10) described above except as otherwise described below. Surgical instrument (100) comprises a handle portion (20), a shaft (22) extending from handle portion (20), and an end effector (12) extending from shaft (22). End effector (12) comprises a lower jaw (16) and an upper jaw in the form of an anvil (18), where anvil (18) is moveable between an open position and a closed, clamped position to clamp tissue between anvil (18) and lower jaw (16). Lower jaw (16) comprises a replaceable staple cartridge (137) that is similar to staple cartridge (37) described above except as described below.

Surgical instrument (100) differs from surgical instrument (10) in that surgical instrument (100) comprises at least one RFID system including a controller (110) having a microprocessor, at least one RFID tag and at least one RFID reader positioned within a proximal end of staple cartridge (137) and/or in a wedge sled (141). Lower jaw (16) includes at least one RFID reader aligned with at least one respective RFID tag (112). The RFID system is configured to operate in the various manners described above, for example to determine whether staple cartridge (137) is properly positioned within lower jaw (16) and/or whether staple cartridge (137) is an appropriate staple cartridge for use with surgical instrument (100).

Figure 9:
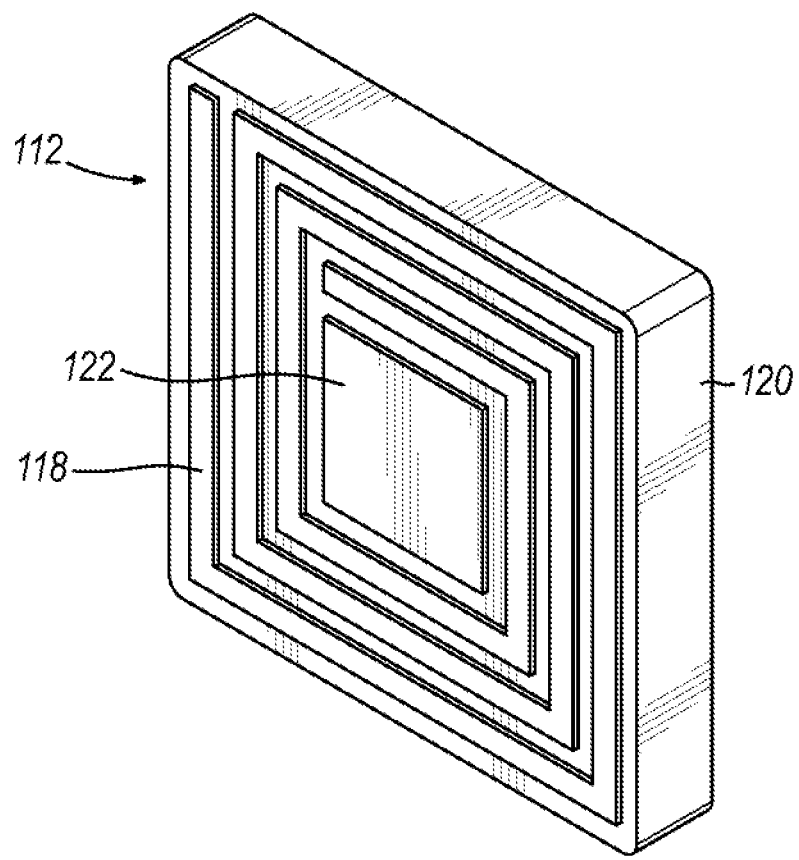
FIG. 9 depicts a perspective view of an exemplary RFID tag.

FIG. 9 shows an exemplary RFID tag (112) in the form of a Hitachi Ultra Small Package UHF RFID tag, although any other suitable RFID tag type could be used in connection with the RFID system of surgical instrument (100). Each RFID tag (112) comprises an antenna (118), an IC chip (122) operatively connected to antenna (118), and a sealing material that seals IC chip (122) and antenna (118). Antenna (118) is constructed of metal and thus may be vulnerable to detuning when RFID tag (112) is placed in contact with a metal surface. IC chip (122) and antenna (118) are mounted to a substrate (120), or base. Antenna (118) is mounted in a circumferential pattern which is in communication with an output channel or pin of IC chip (122). Because RFID tag (112) incorporates an antenna (118) and an IC chip (122) in a single unit, RFID tag (112) is convenient enough to easily affix to any small object using an adhesive or tape, for example. RFID tag (112) may comprise a size of 2.5 mm×2.5 mm×0.4 mm, for example. Additional details regarding RFID tag (112) are disclosed in U.S. Pat. No. 9,171,244, which is incorporated by reference herein in its entirety.

FIGS. 10-14 show a staple cartridge (137) similar to staple cartridge (37) except as otherwise described. Staple cartridge (137) is configured to be removably installed into lower jaw (16) of surgical instrument (100). Staple cartridge (137) comprises a cartridge tray (174) coupled to a cartridge body (170) including an upper deck (72) having staple apertures (51), vertical slot (49), staple drivers (43) and a staple driver actuator in the form of a wedge sled (141).

Staple cartridge (137) differs from staple cartridge (37) in that cartridge body (170) includes a first RFID tag (112a) affixed to a proximal end of cartridge body (170) at a first position (A). Position (A) is proximally located relative to a proximal-most staple aperture (51) of staple apertures (51) and adjacent to a proximal-most end of cartridge body (170). In addition to or in place of first RFID tag (112a), stapler cartridge (137) of the present example further includes a second RFID tag (112b) affixed to wedge sled (141). Wedge sled (141) is slidably positioned within cartridge body (170).

FIG. 11 shows a first RFID reader (114a) and a second RFID reader (114b) positioned within lower jaw (16) of surgical instrument (100). First RFID reader (114a) is integrated into a flexible circuit (124) extending between first RFID reader (114a) and a controller (110) positioned within handle (20) of surgical instrument (100). First RFID reader (114a) comprises a first inductive coil which is configured to longitudinally align with first RFID tag (112a) when staple cartridge (137) is fully seated in lower jaw (16). Second RFID reader (114b) comprises a second inductive coil and is located at a position (B) in lower jaw (16). Second RFID reader (114b) at position (B) is configured to align with second RFID tag (112b) of wedge sled (141) when wedge sled (141) is in a proximal retracted position and when staple cartridge (137) is fully seated in lower jaw (16). In alternative versions, a third RFID tag (not shown) may be coupled to a staple retaining cover (72) of staple cartridge (137) and configured to align with a third RFID reader (not shown) of end effector (12) to ensure that cover (72) is removed after the staple cartridge (137) is fitted within the lower jaw (16). Additionally, it will be understood that various alternative quantities and arrangements of RFID tags and RFID readers may be integrated into select components of end effector (12) in other versions.

When RFID tags (112a, 112b) are in the form of passive RFID tags, each RFID tag (112a, 112b) is configured to emit a signal that is received by its respective RFID reader (114a, 114b). For instance, first RFID reader (114a) may receive a first beacon signal from first RFID tag (112a), and second RFID reader (114b) may receive a second beacon signal from second RFID tag (112b). RFID tags (112a, 112b) can emit beacon signals at the same frequencies or at different frequencies relative to one another. If the beacon signals are emitted at the same frequency, then the range of the beacon signals and/or the position of RFID readers (114a, 114b) must be controlled so that RFID tags (112a, 112b) communicate with their respective RFID readers (114a, 114b). Additionally, RFID tags (112a, 112b) in the form of passive RFID tags may emit signals only in response to being energized by signals received from their respective RFID reader (114a, 114b), which in turn communicates with controller (110). For instance, first RFID tag (112a) does not emit a signal until it is energized by a signal emitted from first reader (114a).

RFID tags (112a, 112b) are operatively secured to cartridge body (170) and to wedge sled (141), respectively, so that RFID tags (112a, 112b) are spaced apart from any metal components of the staple cartridge (137). Various components of staple cartridge (137) may be constructed of metal. For example, cartridge tray (174) and/or a portion of wedge sled (141) may be constructed of steel, aluminum, or various other metals suitable for surgical use. It will be understood that an ordinary passive HF or a UHF RFID tag when directly placed in contact with metal could detune antenna (118), thus preventing the initial signal from RFID readers (114a, 114b) from being received by RFID tags (112a, 112b). Additionally, this metal contact may degrade antenna (118) so that RFID tags (112a, 112b) are unable to produce a return signal. As shown and described herein, staple cartridge (137) is suitably constructed such that each RFID tag (112a, 112b) is spaced apart from, so as to not contact, any adjacent metal portions of staple cartridge (137), thereby enabling RFID tags (112a, 112b) to effectively communicate with RFID readers (114a, 114b).

FIGS. 13-14 show staple cartridge (137) with first RFID tag (112a) positioned within a recess or pocket (126) in a proximate portion of cartridge body (170), which is formed of a plastic. First RFID tag (112a) extends transversely to longitudinal axis (LA) of cartridge body (170). First RFID tag (112a) may be embedded within cartridge body (170) as a result of being over-molded during an injection molding process in which cartridge body (170) is formed of a non-metal, such as plastic, such that an entirety or just a portion of first RFID tag (112a) is encapsulated by cartridge body (170). In yet other versions, a recess, or pocket (126) is formed during the injection molding process and first RFID tag (112a) may be placed within pocket (126) and secured with an adhesive (128) such as an epoxy. A perimeter of first RFID tag (112a) matches a perimeter of pocket (126) such that pocket (126) and first RFID tag (112a) have the same general shape, with pocket (126) being sized slightly larger to receive first RFID tag (112a). Positioning first RFID tag (112a) within cartridge body (170) prevents first RFID tag (112a) from contacting any metal components of surgical instrument (100), such as adjacent metal components of staple cartridge (137) and forming pocket (126) at a location proximal to staple apertures (51) provides additional space within the staple cartridge (170) for additional features and sensors. In still yet other versions, pocket (126) may include a mechanical fastener (not shown) that retains first RFID tag (112a) within pocket (126).

Figure 15:
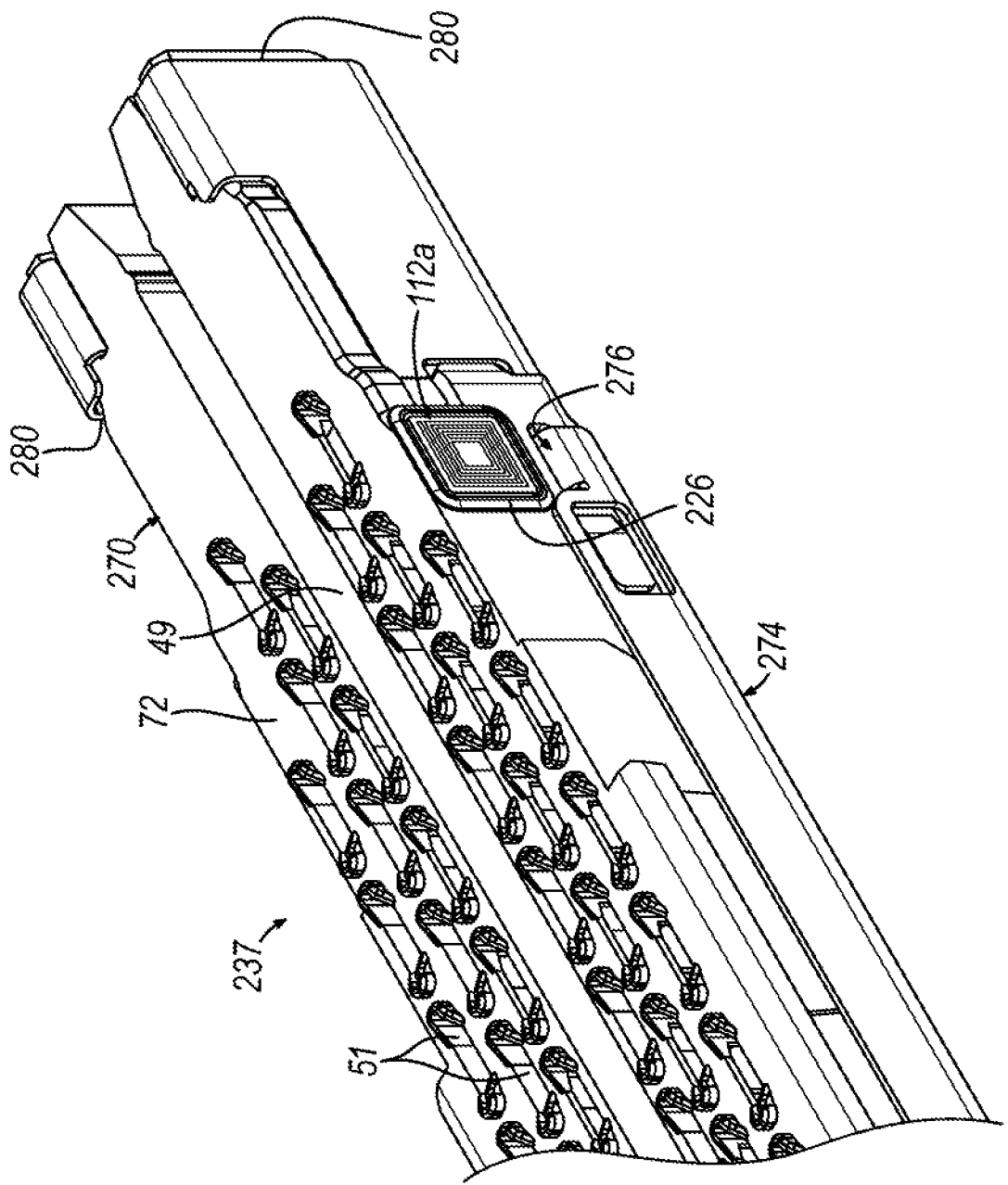
FIG. 15 depicts a side view of another exemplary staple cartridge fitted within a metallic cartridge tray including a cutaway that prevents the metallic cartridge tray from contacting an RFID tag of the type shown in FIG. 9.
Figure 16:
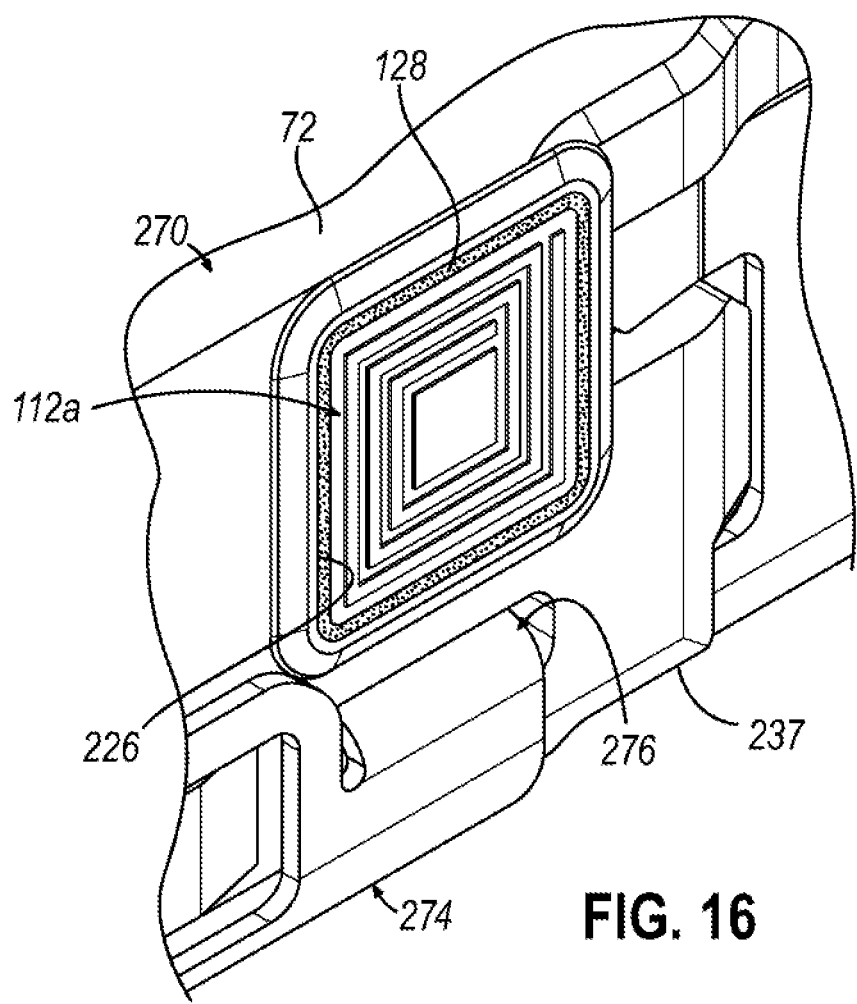
FIG. 16 depicts an enlarged side view of the staple cartridge and the cartridge tray of FIG. 15, showing edges of the tray spaced apart from the RFID tag.

FIGS. 15-16 show staple cartridge (237), which is similar to staple cartridge (137) described above except as otherwise described below. Staple cartridge (237) comprises a cartridge body (270), a wedge sled (141), and a cartridge tray (274). Cartridge body (270) includes an upper deck (72) having staple apertures (51), and vertical slot (49), with staple drivers (43). Wedge sled (141) is movably disposed within cartridge body (270). Cartridge tray (174) is joined with a lower portion of cartridge body (270) and wraps around a pair of external side surfaces of cartridge body (270). Staple cartridge (237), similar to staple cartridge (137), is configured to be removably installed into lower jaw (16) of surgical instrument (100). Both staple cartridges (137, 237) include a first RFID tag (112a) positioned in a proximal portion of cartridge body (170, 270), and a second RFID tag (112b) positioned on wedge sled (141). In other versions, either staple cartridge (137, 237) may include only first RFID tag (112a) or second RFID tag (112b) and may further include one or more additional RFID tags (not shown).

Staple cartridge (237) differs from staple cartridge (137) in the placement and orientation of first RFID tag (112a). Staple cartridge (237) positions first RFID tag (112a) parallel to longitudinal axis (LA) within a recess or a pocket (226) that is recessed within an exterior side surface of cartridge body (270) such that an outer face of first RFID tag (112a) is generally flush with and exposed at the exterior side surface. Pocket (226) extends parallel to longitudinal axis (LA), and first RFID tag (112a) is affixed within pocket (226) with an adhesive (128) such as an epoxy. In some versions, pocket (226) may include a mechanical fastener that is used to retain first RFID tag (112a) in place of or in addition to adhesive (128), or first RFID tag (112a) may be press-fit into pocket (226) without use of adhesive (128). Cartridge tray (274) is operatively coupled to a bottom and an external side surface of cartridge body (270). Cartridge tray (274) is constructed of a metal, such as stainless steel, aluminum, or various other metals suitable for surgical use.

Cartridge tray (274) includes a bottom tray portion (278) and a pair of side tray portions (280) (280) each having a cutaway feature (276). Bottom tray portion (278) is planar and extends along a bottom, or underside, of cartridge body (270). Each side tray portion (280) extends vertically along a respective exterior side surface of cartridge body (270) to removably secure cartridge tray (274) to cartridge body (270). The cutaway feature (276) of each side tray portion (280) is defined by an omission of material and is suitably shaped and located in longitudinal alignment with pocket (226) and first RFID tag (112a) such that side tray portion (280) extends around a perimeter of pocket (226) and is spaced apart from first RFID tag (112a) in a non-contact relationship. As shown best in FIG. 16, cartridge body (270) of the present example further includes a raised ridge on its exterior side surface that extends around the perimeter of pocket (226) to provide an additional, raised barrier between the surrounding edges of side tray portion (280) and RFID tag (112a). Accordingly, cartridge body (270) and cartridge tray (274) are suitably configured to present first RFID tag (112a) at an exterior side surface of cartridge body (270) while ensuring that first RFID tag (112a) is spaced apart from and not in contact with the metallic material of adjacent features of cartridge tray (274). Advantageously, such a configuration protects against detuning of antenna (118) of first RFID tag (112a) and resulting performance-inhibiting effects on communication between first RFID tag (112a) and the respective RFID reader (114a). While only one RFID tag (112a) is shown positioned within a respective pocket (226) on a respective side of cartridge body (270), it will be appreciated that other versions of staple cartridge (237) may feature another RFID tag (112a) positioned on an opposing side of cartridge body (270) within a respective pocket (226), with cartridge body (270) and cartridge tray (274) exhibiting similar features to ensure no contact between cartridge tray (274) and RFID tag (112a).

Figure 17:
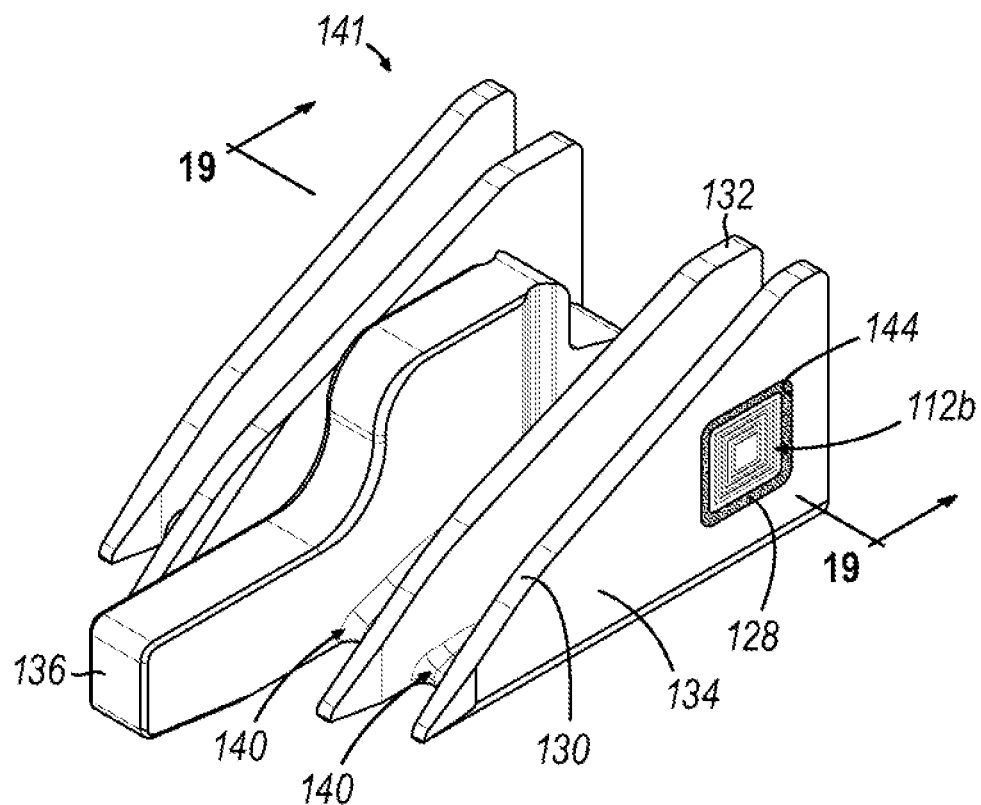
FIG. 17 depicts a perspective view of an exemplary wedge sled that incorporates an RFID tag of the type shown in FIG. 9.
Figure 18:
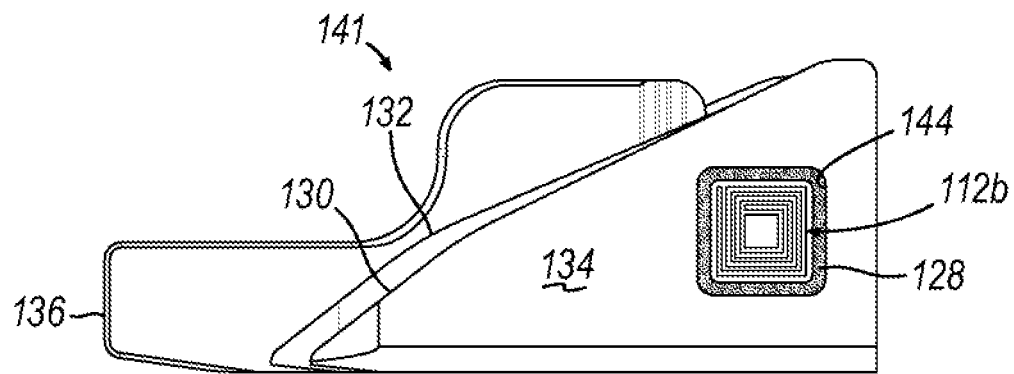
FIG. 18 depicts a side view of the wedge sled of FIG. 17.
Figure 19:
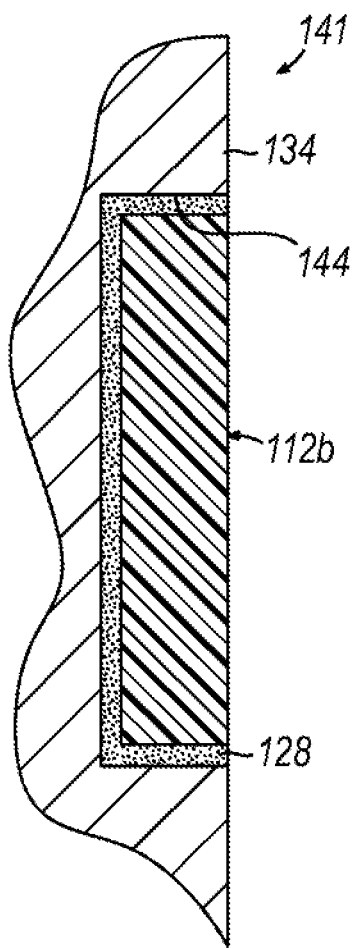
FIG. 19 depicts an enlarged, cross-sectional view of the wedge sled of FIG. 17 that shows additional details of a pocket that retains the RFID tag.

FIGS. 17-19 show a staple driver actuator in the form of a wedge sled (141) that may be movably disposed within staple cartridge bodies (170, 270) similar to wedge sled (41) within staple cartridge body (70). Wedge sled (141) is similar to wedge sled (41) in that wedge sled (141) is moveable longitudinally within staple cartridge (137, 237); while staple drivers (43) are moveable vertically within staple cartridge (137, 237). Wedge sled (141) includes a plurality of cam surfaces configured to urge staple drivers

(43) upwardly as wedge sled (141) is driven distally through staple cartridge (137, 237). These cam surfaces are defined by an outer pair of laterally-opposed rails (134) and an inner pair of laterally-opposed rails (132). Wedge sled (141) further includes a central body (136) positioned between inner pair of laterally-opposed rails (132) and linking members (140) and that extends distally from a medial upright section having a first maximum height to a tapered distal nose section having a shorter second height. Linking members (140) affix outer pair of laterally-opposed rails (134) to inner pair of laterally-opposed rails (132) and inner pair of laterally-opposed rails (132) to central body (136). Central body (136) is configured to longitudinally translate through slot (49) of cartridge body (170, 270), along longitudinal axis (LA), when staple cartridge (137, 237) is fired on tissue.

Wedge sled (141) differs from wedge sled (41) in that at least a portion of wedge sled (141) is constructed of metal such as stainless steel, aluminum, or another metal suitable for surgical use. In the present version, outer rails (134) are constructed of metal and at least one of outer rails (134) includes a recess or pocket (144) formed in its exterior side surface. Second RFID tag (112b) is positioned within pocket (144) such that an outer face of second RFID tag (112b) is generally flush with and exposed at the exterior side surface of outer rail (134). By positioning second RFID tag (112b) at an exterior surface of outer rail (134), a gap distance between second RFID tag (112b) and its respective RFID reader (114b) within lower jaw (16) of instrument (100) is minimized, thereby strengthening the exchanged signals. A perimeter of pocket (144) matches a perimeter of second RFID tag (112b) such that pocket (144) and second RFID tag (112b) have the same general shape, with pocket (144) being sized slightly larger to receive second RFID tag (112b).

Second RFID tag (112b) is secured within pocket (144) by an adhesive (128), which may be in the form of an epoxy, that separates second RFID tag (112b) from all confronting metallic surfaces of outer rail (134). Adhesive (128) includes electrically-insulating properties (i.e., is non-electrically conductive) that act as an electrically-insulative barrier between metallic outer rail (134) and second RFID tag (112b). Accordingly, by occupying a space between second RFID tag (112b) and confronting surfaces of outer rail (134), and by having electrically-insulative properties, adhesive (128) prevents metallic outer rail (134) from detuning an antenna (118) of second RFID tag (112b), thereby enabling consistent and reliable communication between second RFID tag (112b) and second RFID reader (114b). Second RFID tag (112b) is configured to communicate with second RFID reader (114b) and optionally one or more additional RFID readers (not shown) positioned within lower jaw (16) so that controller (110) may determine a longitudinal position of wedge sled (141) within cartridge body (170, 270) before, during, and/or after completion of a firing stroke. In the present version, pocket (144) and second RFID tag (112b) are oriented parallel to longitudinal axis (LA), though it will be appreciated that pocket (144) and second RFID tag (112b) may be oriented in various other ways relative to longitudinal axis (LA) in other versions of wedge sled (141).

In some versions, surgical instrument (100) may include second RFID tag (112b) and omit first RFID tag (112a), or vice-versa. The qualifiers "first" and "second" are not meant to be limiting in any way and are merely reference labels that provide a way to differentiate RFID tags (112a, 112b) in the present disclosure.

Figure 20:
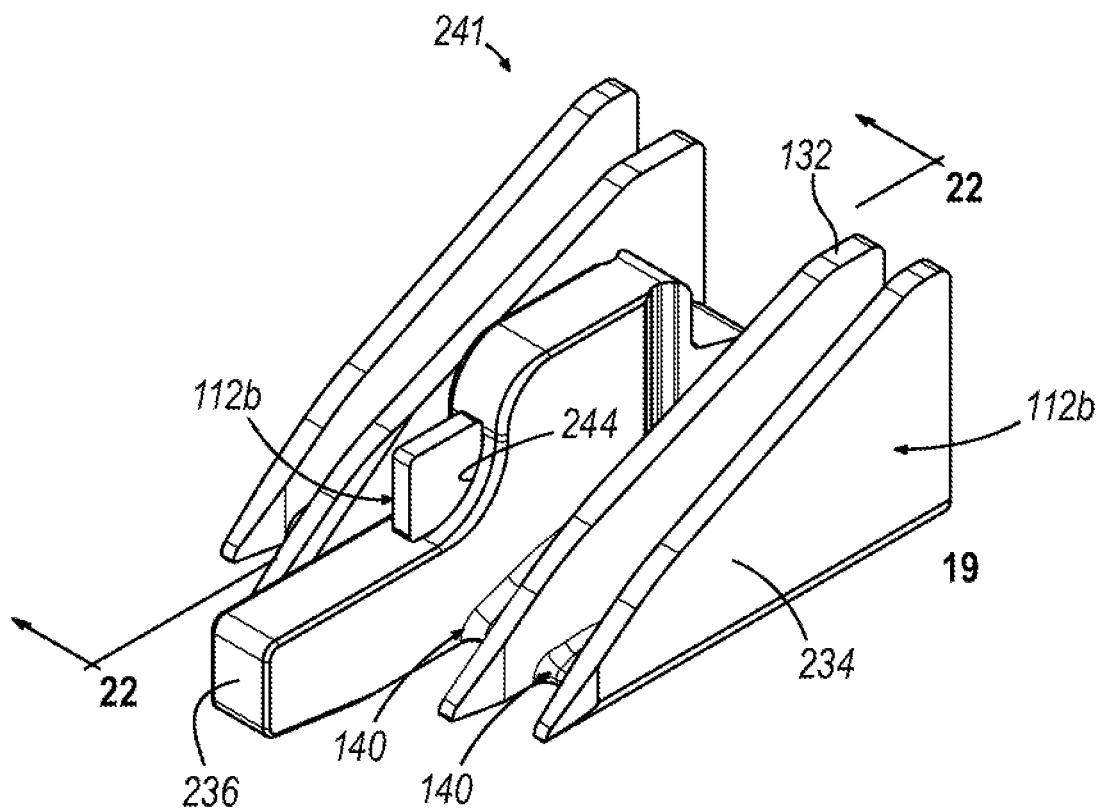
FIG. 20 depicts a perspective view of another exemplary wedge sled that incorporates an RFID tag of the type shown in FIG. 9.
Figure 21:
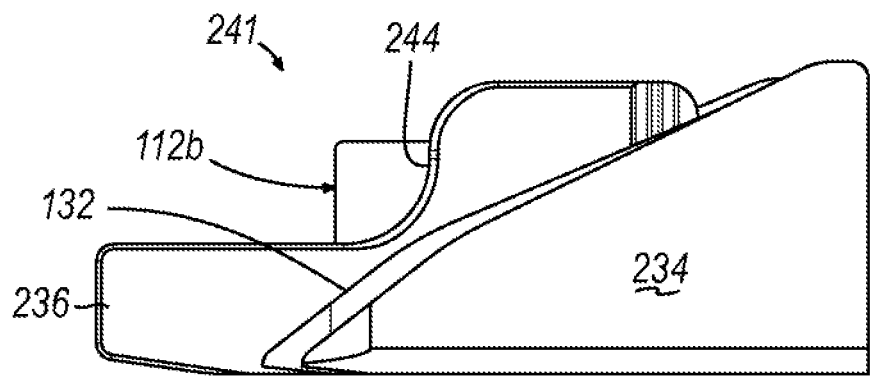
FIG. 21 depicts a side view of the wedge sled of FIG. 20.
Figure 22:
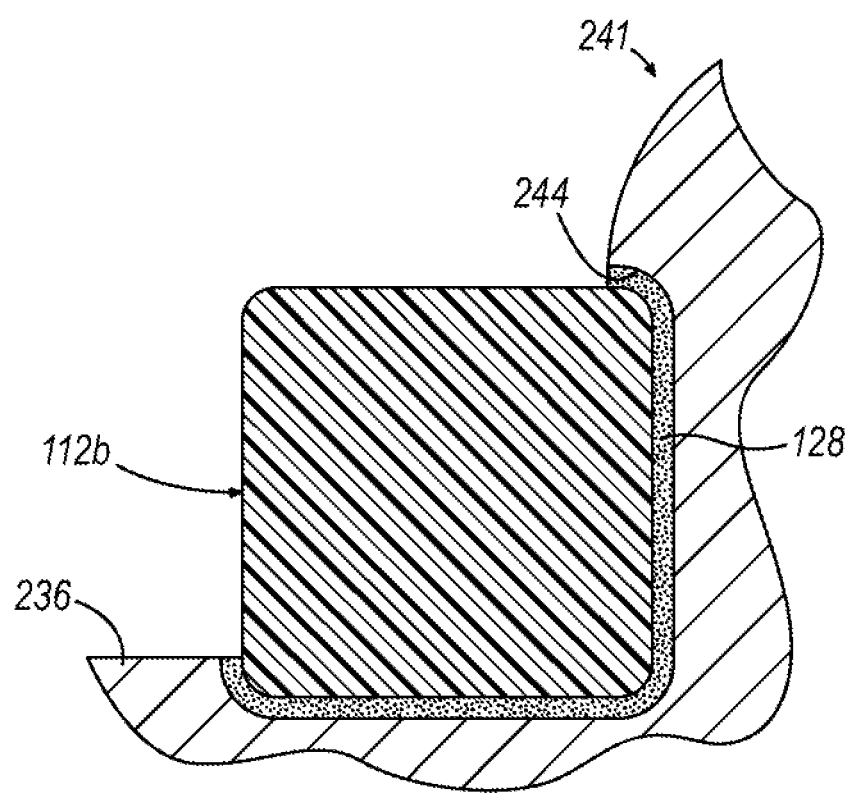
FIG. 22 depicts an enlarged, cross-sectional view of the wedge sled of FIG. 20 that shows additional details of a pocket that retains the RFID tag.

FIGS. 20-22 show another exemplary staple driver actuator in the form of a wedge sled (241) that is similar to wedge sled (141) except as otherwise described below and that is configured for use with staple cartridges (137, 237). Wedge sled (241) includes a plurality of cam surfaces defined by an outer pair of laterally-opposed pair of rails (234) and an inner pair of laterally-opposed rails (132). Wedge sled (241) further includes a central body (236) similar to central body (136) and positioned between inner pair of laterally-opposed rails (132) and linking members (140). Linking members (140) couple inner and outer pairs of laterally-opposed rails (132, 234) together and couple inner pair of laterally-opposed rails (132) to central body (236). Similar to wedge sled (141), at least a portion of wedge sled (241) is constructed of metal such as stainless steel, aluminum, or another metal suitable for surgical applications. Wedge sled (241) differs from wedge sled (141) in that second RFID tag (112b) is affixed to central body (236) within a distally facing recess or pocket (244) formed in central body (236), and pocket (244) is configured to retain second RFID tag (112b). In the present version, pocket (244) is located at the junction between the upright medial section and the tapered distal nose section of central body (236). In other versions, pocket (244) and second RFID tag (112b) may be positioned at various other locations along the length of central body (236). At least a portion of central body (236) in the present version is constructed of metal such as stainless steel, aluminum, or another metal suitable for surgical use, and second RFID tag (112b) is affixed to central body (236) within pocket (244) using an adhesive (128), which may be in the form of an epoxy. As described above in connection with wedge sled (141), adhesive (128) has the dual function of retaining second RFID tag (112b) within pocket (244) and electrically-insulating second RFID tag (112b) from confronting metallic surfaces of central body (236) so that metallic central body (236) does not detune antenna (118) of second RFID tag (112b), thereby enabling consistent and reliable communication between second RFID tag (112b) and second RFID reader (114b).

In other versions, at least the portion of central body (236) that retains second RFID tag (112b) may be constructed of a non-metal, such as a plastic, such that second RFID tag (112b) may be positioned in direct contact with central body (236) without detuning antenna (118) of second RFID tag (112b). For instance, in some versions, an entirety or just a portion of central body (236) may be injection molded of a non-metallic material over a portion of second RFID tag (112b), or second RFID tag (112b) may be attached to central body (236) after the non-metallic portion of central body (236) is formed. In some such versions, a remaining portion of wedge sled (241) may be constructed of metal, such as inner pair of laterally-opposed rails (132), outer laterally-opposed pair of rails (234), or both inner and outer pairs of laterally-opposed rails (132, 234). In such versions, the non-metal construction of central body (236) may electrically insulate second RFID tag (112b) from any metal portions of wedge sled (241).

It will be appreciated that any of the concepts disclosed herein in connection with wedge sleds (41, 141, 241) may be combined with any one or more teachings of U.S. patent application Ser. No. 17/088,941, entitled "Surgical Staple End Effector Sled Having Cartridge Wall Support Feature," filed Nov. 4, 2020, issued as U.S. Pat. No. 11,540,826 on Jan. 3, 2023, the disclosure of which is incorporated by reference herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A staple cartridge comprising: (a) a cartridge body defining a longitudinal axis extending from a proximal end to a distal end of the cartridge body and configured to be received within a jaw of a surgical stapler, wherein the cartridge body defines a plurality of staple apertures configured to house staples, wherein a proximal portion of the cartridge body defines a pocket, wherein the pocket is proximal to a proximal most staple aperture of the plurality of staple apertures; and (b) a first RFID feature fixed within the pocket, wherein the first RFID feature is configured to communicate with a second RFID feature presented by the jaw of the surgical stapler.

Example 2

The staple cartridge of Example 1, wherein the first RFID feature comprises an RFID tag, wherein the second RFID feature comprises an RFID reader.

Example 3

The staple cartridge of any of the previous Examples, wherein the first RFID feature extends parallel to the longitudinal axis.

Example 4

The staple cartridge of any of the previous Examples, wherein the pocket is positioned on an external side surface of the cartridge body and the first RFID feature is fixed within the pocket with an adhesive.

Example 5

The staple cartridge of any of the previous Examples, further comprising a cartridge tray coupled to an underside of the cartridge body, wherein the cartridge tray is constructed of metal, wherein the cartridge tray is shaped so that the cartridge tray does not contact the first RFID feature.

Example 6

The staple cartridge of Example 5, wherein the cartridge tray includes a cutaway feature configured to provide a spacing between the first RFID feature and the cartridge tray.

Example 7

The staple cartridge of any of the previous Examples, wherein the first RFID feature is embedded within the proximal portion of the cartridge body and extends transversely to the longitudinal axis.

Example 8

The staple cartridge of any of the previous Examples, wherein the first RFID feature is secured within the proximal end of the cartridge body with an adhesive.

Example 9

A surgical stapler, comprising: (a) the staple cartridge of any of the previous Examples; (b) a first jaw configured to receive the staple cartridge, wherein the second RFID feature is positioned within the first jaw; and (c) a second jaw that includes an anvil, wherein the first and second jaws are configured to cooperate to clamp and staple tissue therebetween.

Example 10

The surgical stapler of Example 9, wherein the staple cartridge further comprises: (a) a plurality of staple drivers configured to drive the staples from the staple apertures; and (b) a staple driver actuator, wherein the staple driver actuator includes: (i) a plurality of rails configured to cammingly engage the plurality of staple drivers during translation of the staple driver actuator along the longitudinal axis, and (ii) a central body.

Example 11

The surgical stapler of Example 10, wherein the first RFID feature includes a first RFID tag and the second RFID feature includes a first RFID reader configured to communicate with the first RFID tag, wherein the surgical stapler further comprises a second RFID tag positioned on the staple driver actuator and a second RFID reader positioned within the first jaw, wherein the second RFID tag is configured to communicate with the second RFID reader.

Example 12

The surgical stapler of Example 11, wherein the staple driver actuator includes a metal portion, wherein the second RFID tag is spaced apart from the metal portion to thereby inhibit direct contact between the second RFID tag and the metal portion.

Example 13

The surgical stapler of Example 12, wherein the central body includes the metal portion, wherein the second RFID tag is affixed to the central body such that the second RFID tag is spaced apart from the metal portion.

Example 14

The surgical stapler of Examples 12 through 13, wherein an outermost rail of the plurality of rails includes the metal portion, wherein the second RFID tag is affixed to the outermost rail such that the second RFID tag is spaced apart from the metal portion.

Example 15

The surgical stapler of Examples 12 through 14, wherein the metal portion of the staple driver actuator includes a recess, wherein the second RFID tag is fixed within the recess.

Example 16

An apparatus comprising: (a) a first jaw, wherein the first jaw defines a longitudinal axis; (b) a second jaw that includes an anvil, wherein the first and second jaws are movable relative to one another to clamp tissue; and (c) a cartridge, wherein the cartridge is insertable into the first jaw, wherein the cartridge comprises: (i) a plurality of staples, (ii) a plurality of staple drivers actuatable to drive the staples into the clamped tissue, (iii) a staple driver actuator including a metal portion, wherein the staple driver actuator comprises: (A) a pair of laterally-opposed rails configured to cammingly engage respective staple drivers of the plurality of staple drivers during translation of the staple driver actuator along the longitudinal axis, and (B) a central body, and (iv) an RFID tag affixed to the staple driver actuator and spaced apart from the metal portion.

Example 17

The apparatus of Example 16, wherein the central body includes the metal portion, wherein the metal portion has a pocket, wherein the RFID tag is affixed within the pocket with an adhesive, wherein the adhesive is configured to electrically insulate the RFID tag from the metal portion.

Example 18

The apparatus of any of the Examples 16 through 17, wherein the pair of laterally-opposed rails includes the metal portion, wherein the metal portion has a pocket, wherein the RFID tag is affixed within the pocket with an adhesive, wherein the adhesive is configured to electrically insulate the RFID tag from the metal portion.

Example 19

An apparatus comprising: (a) a first jaw defining a longitudinal axis and including an RFID reader; (b) a second jaw including an anvil, wherein the first and second jaws are configured to cooperate to clamp tissue; and (c) a staple cartridge insertable into the first jaw, wherein the staple cartridge comprises: (i) a cartridge body, (ii) a plurality of staples, (iii) a plurality of staple drivers actuatable to drive the staples into the clamped tissue, (iv) a metallic cartridge tray configured to cover a portion of the cartridge body, and (v) an RFID tag positioned at a proximal end of the cartridge body and spaced apart from the metallic cartridge tray, wherein the RFID tag is configured to communicate with the RFID reader.

Example 20

The apparatus of Example 19, wherein the RFID tag is exposed at an outer surface of the cartridge body, wherein a proximal tray portion of the metallic cartridge tray includes a cutaway feature such that the proximal tray portion extends along at least a portion of a perimeter of the RFID tag without contacting the RFID tag.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they may be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A staple cartridge comprising:
   (a) a cartridge body configured to be received within a jaw of a surgical stapler, wherein the cartridge body defines a plurality of staple apertures configured to house staples, wherein a proximal portion of the cartridge body defines a pocket at a location proximal to a proximal-most staple aperture of the plurality of staple apertures;
   a plurality of staple drivers actuatable to drive the staples from the staple apertures;
   (c) a staple driver actuator including a metal portion and having a plurality of rails configured to cammingly actuate the staple drivers as the staple driver actuator advances through the cartridge body, wherein an outermost rail of the plurality of rails includes a recess;
   (d) a first RFID tag fixed within the pocket of the cartridge body; and
   (e) a second RFID tag fixed within the recess of the staple driver actuator, and spaced apart from the metal portion.

2. The staple cartridge of claim 1, wherein the first RFID tag includes a length and a width that define a plane that extends parallel to a longitudinal axis of the cartridge body.

3. The staple cartridge of claim 1, wherein the pocket is positioned on an external side surface of the cartridge body and the first RFID tag is fixed within the pocket with an adhesive.

4. The staple cartridge of claim 1, further comprising a cartridge tray coupled to an underside of the cartridge body, wherein the cartridge tray is constructed of metal, wherein the cartridge tray is shaped so that the cartridge tray does not contact the first RFID tag.

5. The staple cartridge of claim 4, wherein the cartridge tray includes a cutaway configured to provide a spacing between the first RFID tag and the cartridge tray.

6. The staple cartridge of claim 1, wherein the first RFID tag is embedded within the proximal portion of the cartridge body and includes a length and a width that define a plane that extends transversely to a longitudinal axis of the cartridge body.

7. The staple cartridge of claim 1, wherein the first RFID tag is secured within the proximal portion of the cartridge body with an adhesive.

8. A surgical stapler, comprising:
   (a) the staple cartridge of claim 1;
   (b) a first jaw configured to receive the staple cartridge and including an RFID reader configured to communicate with at least one of the first RFID tag or the second RFID tag; and
   (c) a second jaw that includes an anvil, wherein the first and second jaws are configured to cooperate to clamp and staple tissue therebetween.

9. The surgical stapler of claim 8, wherein the RFID reader comprises a first RFID reader configured to communicate with the first RFID tag, wherein the surgical stapler further comprises a second RFID reader positioned within the first jaw and configured to communicate with the second RFID tag.

10. The surgical stapler of claim 9, wherein the staple driver actuator includes a metal portion, wherein the second RFID tag is affixed to the staple driver actuator such that the second RFID tag is spaced apart from the metal portion.

11. The surgical stapler of claim 10, wherein the outermost rail of the plurality of rails includes the metal portion.

12. The apparatus of claim 1, wherein the pocket is disposed in the proximally facing end wall of the cartridge body, wherein the first RFID tag is fixed within the pocket such that a length and a width of the first RFID tag define a plane that extends transversely to a longitudinal axis of the cartridge body.

13. An apparatus comprising:
   (a) a first jaw, wherein the first jaw defines a longitudinal axis;
   (b) a second jaw that includes an anvil, wherein the first and second jaws are movable relative to one another to clamp tissue; and
   (c) a cartridge, wherein the cartridge is insertable into the first jaw, wherein the cartridge comprises:
      (i) a plurality of staples,
      (ii) a plurality of staple drivers actuatable to drive the staples into the clamped tissue,
      (iii) a staple driver actuator including a metal portion, wherein the staple driver actuator comprises:
         (A) a plurality of rails configured to cammingly engage respective staple drivers of the plurality of staple drivers during translation of the staple driver actuator along the longitudinal axis and including an outermost rail that at least partially defines the metal portion and has a pocket, and
         (B) a central body, and
      (iv) an RFID tag affixed within the pocket of the outermost rail of the staple driver actuator and spaced apart from the metal portion.

14. The apparatus of claim 13, wherein the RFID tag is affixed within the pocket with an adhesive configured to electrically insulate the RFID tag from the metal portion.

15. An apparatus comprising:
   (a) a first jaw including an RFID reader;
   (b) a second jaw including an anvil, wherein the first and second jaws are configured to cooperate to clamp tissue; and
   (c) a staple cartridge insertable into the first jaw, wherein the staple cartridge comprises:
      (i) a cartridge body,
      (ii) a plurality of staples,
      (iii) a plurality of staple drivers actuatable to drive the staples into the clamped tissue,
      (iv) a metallic cartridge tray configured to cover an underside of the cartridge body, wherein a proximal tray portion of the metallic cartridge tray includes a cutaway positioned along a laterally outermost sidewall of the cartridge body, and
      (v) an RFID tag recessed within the laterally outermost sidewall of the cartridge body and in alignment with the cutaway of the proximal tray portion such that the proximal tray portion overlies a proximal wall portion of the laterally outermost sidewall without overlying the RFID tag, wherein the RFID tag is configured to communicate with the RFID reader.

16. The apparatus of claim 15, wherein the RFID tag is exposed at a substantially vertically extending outer surface of the laterally outermost sidewall of the cartridge body.

* * * * *